(12) United States Patent
McCormack

(10) Patent No.: US 7,824,431 B2
(45) Date of Patent: Nov. 2, 2010

(54) CERVICAL DISTRACTION METHOD

(75) Inventor: Bruce McCormack, San Francisco, CA (US)

(73) Assignee: Providence Medical Technology, Inc., San Francisco, CA (US)

( * ) Notice: Subject to any disclaimer, the term of this patent is extended or adjusted under 35 U.S.C. 154(b) by 0 days.

(21) Appl. No.: 12/110,548

(22) Filed: Apr. 28, 2008

(65) Prior Publication Data

US 2008/0208341 A1 Aug. 28, 2008

Related U.S. Application Data

(62) Division of application No. 11/618,619, filed on Dec. 29, 2006, now abandoned.

(51) Int. Cl.
*A61B 17/88* (2006.01)
(52) U.S. Cl. .................................................. 606/279
(58) Field of Classification Search ............... 606/247; 623/17.11–17.16
See application file for complete search history.

(56) References Cited

U.S. PATENT DOCUMENTS

| | | |
|---|---|---|
| 4,479,491 A | 10/1984 | Martin |
| 4,530,355 A | 7/1985 | Griggs |
| 4,772,287 A | 9/1988 | Ray et al. |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,236,460 A | 8/1993 | Barber ............... 623/17.15 |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich ............... 623/17.12 |
| 5,571,191 A | 11/1996 | Fitz |
| 5,593,409 A | 1/1997 | Michelson |
| 5,632,747 A | 5/1997 | Scarborough et al. |
| 5,674,295 A | 10/1997 | Ray et al. ............... 623/17.12 |
| 5,720,748 A | 2/1998 | Kuslich et al. |
| 5,741,253 A | 4/1998 | Michelson |
| 5,772,661 A | 6/1998 | Michelson |
| 5,797,909 A | 8/1998 | Michelson |

(Continued)

FOREIGN PATENT DOCUMENTS

DE G 93 04 368.6 5/2003

(Continued)

OTHER PUBLICATIONS

Non-Final Office Action and PTO-892, U.S. Appl. No. 11/618,619, mailed Jan. 3, 2008, 12 pages.

(Continued)

*Primary Examiner*—Anu Ramana
(74) *Attorney, Agent, or Firm*—Dorsey & Whitney LLP

(57) ABSTRACT

A device and method for a minimally invasive surgical implantation to reduce radicular symptoms by inserting an expandable cervical distraction implant in the facet joint and distracting the adjacent cervical vertebrae to increase the foraminal dimension. The implant, when positioned in the cervical facet joint, expands via delivery of an inflation medium to increase the space between the vertebrae, thereby increasing the foraminal area or dimension, and reducing pressure on the nerves and blood vessels of the cervical spine.

8 Claims, 4 Drawing Sheets

U.S. PATENT DOCUMENTS

| | | | |
|---|---|---|---|
| 5,836,948 A | 11/1998 | Zuckerman et al. | |
| 5,879,353 A | 3/1999 | Terry | |
| 5,885,299 A | 3/1999 | Winslow et al. | |
| 5,891,147 A | 4/1999 | Moskovitz et al. | |
| 5,895,426 A | 4/1999 | Scarborough et al. | |
| 5,899,908 A | 5/1999 | Kuslich et al. | |
| 5,928,238 A | 7/1999 | Scarborough et al. | |
| 5,961,522 A | 10/1999 | Mehdizadeh | |
| 5,976,146 A | 11/1999 | Ogawa et al. | |
| 6,033,405 A | 3/2000 | Winslow et al. | |
| 6,045,580 A | 4/2000 | Scarborough et al. | |
| 6,063,088 A | 5/2000 | Winslow | |
| RE36,758 E | 6/2000 | Fitz | |
| 6,080,155 A | 6/2000 | Michelson | |
| 6,096,038 A | 8/2000 | Michelson | |
| 6,099,531 A | 8/2000 | Bonutti | |
| 6,149,650 A | 11/2000 | Michelson | |
| RE37,005 E | 12/2000 | Michelson et al. | |
| 6,190,388 B1 | 2/2001 | Michelson et al. | |
| 6,190,414 B1 | 2/2001 | Young et al. | |
| 6,210,412 B1 | 4/2001 | Michelson | |
| RE37,161 E | 5/2001 | Michelson et al. | |
| 6,224,595 B1 | 5/2001 | Michelson | |
| 6,224,607 B1 | 5/2001 | Michelson | |
| 6,224,630 B1 * | 5/2001 | Bao et al. | 623/17.16 |
| 6,248,110 B1 | 6/2001 | Reiley et al. | 606/93 |
| 6,264,656 B1 | 7/2001 | Michelson | |
| 6,267,763 B1 | 7/2001 | Castro | |
| 6,270,498 B1 | 8/2001 | Michelson | |
| 6,283,966 B1 | 9/2001 | Houfburg | |
| 6,315,795 B1 | 11/2001 | Scarborough et al. | |
| 6,402,784 B1 | 6/2002 | Wardlaw | 623/17.11 |
| 6,423,063 B1 | 7/2002 | Bonutti | |
| 6,423,083 B2 | 7/2002 | Reiley et al. | 606/192 |
| 6,425,919 B1 | 7/2002 | Lambrecht | |
| 6,436,098 B1 | 8/2002 | Michelson | |
| 6,443,988 B2 | 9/2002 | Felt et al. | 623/17.12 |
| 6,451,023 B1 | 9/2002 | Salazar et al. | |
| 6,478,796 B2 | 11/2002 | Zucherman et al. | |
| 6,500,206 B1 | 12/2002 | Bryan | |
| 6,514,256 B2 | 2/2003 | Zucherman et al. | |
| 6,565,574 B2 | 5/2003 | Michelson | |
| 6,569,186 B1 | 5/2003 | Winters et al. | |
| 6,575,919 B1 | 6/2003 | Reiley et al. | |
| 6,579,319 B2 | 6/2003 | Goble et al. | |
| 6,582,432 B1 | 6/2003 | Michelson | |
| 6,607,530 B1 | 8/2003 | Carl et al. | |
| 6,610,091 B1 | 8/2003 | Reiley | |
| 6,626,905 B1 | 9/2003 | Schmiel et al. | |
| 6,632,235 B2 | 10/2003 | Weikel et al. | 606/192 |
| 6,635,060 B2 | 10/2003 | Hanson et al. | |
| 6,641,582 B1 | 11/2003 | Hanson et al. | |
| 6,648,893 B2 | 11/2003 | Dudasik | |
| 6,652,584 B2 | 11/2003 | Michelson | |
| 6,663,647 B2 | 12/2003 | Reiley et al. | 606/192 |
| 6,666,866 B2 | 12/2003 | Martz et al. | |
| 6,679,886 B2 | 1/2004 | Weikel et al. | |
| 6,682,535 B2 | 1/2004 | Hoogland | |
| 6,709,458 B2 | 3/2004 | Michelson | |
| 6,712,853 B2 | 3/2004 | Kuslich | |
| 6,719,773 B1 | 4/2004 | Boucher et al. | |
| 6,723,095 B2 | 4/2004 | Hammerslag | |
| 6,740,093 B2 | 5/2004 | Hochschuler et al. | 606/94 |
| 6,770,074 B2 | 8/2004 | Michelson | |
| 6,793,679 B2 | 9/2004 | Michelson | |
| 6,805,715 B2 | 10/2004 | Reuter et al. | 623/17.12 |
| 6,808,537 B2 | 10/2004 | Michelson | |
| 6,875,213 B2 | 4/2005 | Michelson | |
| 6,899,719 B2 | 5/2005 | Reiley et al. | 606/192 |
| 6,921,403 B2 | 7/2005 | Cragg et al. | |
| 6,923,813 B2 | 8/2005 | Phillips et al. | |
| 6,962,606 B2 | 11/2005 | Michelson | |
| 6,966,930 B2 | 11/2005 | Arnin et al. | |
| 6,972,035 B2 | 12/2005 | Michelson | |
| 6,979,333 B2 | 12/2005 | Hammerslag | |
| 7,001,385 B2 | 2/2006 | Bonutti | |
| 7,008,453 B1 | 3/2006 | Michelson | |
| 7,033,362 B2 | 4/2006 | McGahan et al. | |
| 7,033,392 B2 | 4/2006 | Schmiel et al. | |
| 7,066,961 B2 | 6/2006 | Michelson | |
| 7,083,623 B2 | 8/2006 | Michelson | |
| 7,101,398 B2 | 9/2006 | Dooris et al. | |
| 7,115,128 B2 | 10/2006 | Michelson | |
| 7,118,598 B2 | 10/2006 | Michelson | |
| 7,128,760 B2 | 10/2006 | Michelson | |
| 7,207,991 B2 | 4/2007 | Michelson | |
| 7,264,622 B2 | 9/2007 | Michelson | |
| 7,288,093 B2 | 10/2007 | Michelson | |
| 7,291,149 B1 | 11/2007 | Michelson | |
| 7,300,440 B2 | 11/2007 | Zdeblick et al. | |
| 7,326,211 B2 | 2/2008 | Padget et al. | |
| 7,326,214 B2 | 2/2008 | Michelson | |
| 7,371,238 B2 | 5/2008 | Soboleski et al. | |
| 7,399,303 B2 | 7/2008 | Michelson | |
| 7,410,501 B2 | 8/2008 | Michelson | |
| 7,431,722 B1 | 10/2008 | Michelson | |
| 7,445,636 B2 | 11/2008 | Michelson | |
| 7,452,359 B1 | 11/2008 | Michelson | |
| 7,452,369 B2 | 11/2008 | Barry | |
| 7,465,304 B1 | 12/2008 | Haufe et al. | |
| 7,479,160 B2 | 1/2009 | Branch et al. | |
| 7,491,205 B1 | 2/2009 | Michelson | |
| 7,569,054 B2 | 8/2009 | Michelson | |
| 7,648,523 B2 | 1/2010 | Mirkovic et al. | |
| 7,686,807 B2 | 3/2010 | Padget et al. | |
| 7,708,761 B2 | 5/2010 | Petersen | |
| 2001/0004710 A1 | 6/2001 | Felt et al. | 623/17.12 |
| 2002/0026195 A1 | 2/2002 | Layne et al. | |
| 2002/0107519 A1 | 8/2002 | Dixon et al. | |
| 2002/0143343 A1 | 10/2002 | Castro | |
| 2002/0147496 A1 | 10/2002 | Belef et al. | 623/17.12 |
| 2002/0147497 A1 | 10/2002 | Belef et al. | 623/17.12 |
| 2002/0169471 A1 | 11/2002 | Ferdinand | |
| 2003/0028251 A1 | 2/2003 | Mathews | 623/17.16 |
| 2003/0033017 A1 | 2/2003 | Lotz et al. | 623/17.16 |
| 2003/0139816 A1 | 7/2003 | Michelson | |
| 2003/0144737 A1 | 7/2003 | Sherman | 623/17.12 |
| 2003/0158553 A1 | 8/2003 | Michelson | |
| 2003/0158557 A1 | 8/2003 | Cragg et al. | |
| 2003/0199983 A1 | 10/2003 | Michelson | |
| 2004/0059337 A1 | 3/2004 | Hanson et al. | |
| 2004/0073217 A1 | 4/2004 | Michelson | |
| 2004/0087948 A1 | 5/2004 | Suddaby | |
| 2004/0087956 A1 | 5/2004 | Weikel et al. | |
| 2004/0093084 A1 | 5/2004 | Michelson | |
| 2004/0106999 A1 | 6/2004 | Mathews | 623/17.16 |
| 2004/0133208 A1 | 7/2004 | Weikel et al. | |
| 2004/0133277 A1 | 7/2004 | Michelson | |
| 2004/0133280 A1 | 7/2004 | Trieu | |
| 2004/0148029 A1 | 7/2004 | Bianchi et al. | |
| 2004/0162562 A1 | 8/2004 | Martz | |
| 2004/0215344 A1 | 10/2004 | Hochschuler et al. | 623/17.12 |
| 2004/0236331 A1 | 11/2004 | Michelson | |
| 2005/0010294 A1 | 1/2005 | Michelson | |
| 2005/0015149 A1 | 1/2005 | Michelson | |
| 2005/0027358 A1 | 2/2005 | Suddaby | 623/17.11 |
| 2005/0049705 A1 | 3/2005 | Hale et al. | |
| 2005/0055096 A1 | 3/2005 | Serhan et al. | |
| 2005/0060037 A1 | 3/2005 | Michelson | |
| 2005/0065518 A1 | 3/2005 | Michelson | |
| 2005/0065519 A1 | 3/2005 | Michelson | |
| 2005/0065529 A1 | 3/2005 | Liu et al. | |
| 2005/0065608 A1 | 3/2005 | Michelson | |
| 2005/0065609 A1 | 3/2005 | Wardlaw | 623/17.12 |

| | | |
|---|---|---|
| 2005/0080422 A1 | 4/2005 | Otte et al. |
| 2005/0090829 A1 | 4/2005 | Martz et al. |
| 2005/0090901 A1 | 4/2005 | Studer .................... 623/17.12 |
| 2005/0113929 A1 | 5/2005 | Cragg et al. |
| 2005/0119660 A1 | 6/2005 | Bourlion et al. |
| 2005/0119680 A1 | 6/2005 | Dykes |
| 2005/0124993 A1 | 6/2005 | Chappuis |
| 2005/0154460 A1 | 7/2005 | Yundt |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0216018 A1 | 9/2005 | Sennett |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0261695 A1 | 11/2005 | Cragg et al. |
| 2005/0267480 A1 | 12/2005 | Suddaby |
| 2006/0004367 A1 | 1/2006 | Alamin et al. |
| 2006/0036243 A1 | 2/2006 | Sasso et al. |
| 2006/0036247 A1 | 2/2006 | Michelson |
| 2006/0036323 A1* | 2/2006 | Carl et al. ................. 623/17.11 |
| 2006/0041311 A1 | 2/2006 | McLeer |
| 2006/0058793 A1 | 3/2006 | Michelson |
| 2006/0058878 A1 | 3/2006 | Michelson |
| 2006/0064099 A1 | 3/2006 | Pavlov et al. |
| 2006/0064100 A1 | 3/2006 | Bertagnoli et al. |
| 2006/0069442 A1 | 3/2006 | Michelson |
| 2006/0079905 A1 | 4/2006 | Beyar et al. |
| 2006/0079962 A1 | 4/2006 | Michelson |
| 2006/0084992 A1 | 4/2006 | Michelson |
| 2006/0085068 A1 | 4/2006 | Barry |
| 2006/0085074 A1* | 4/2006 | Raiszadeh ................. 623/17.12 |
| 2006/0095028 A1 | 5/2006 | Bleich |
| 2006/0095036 A1 | 5/2006 | Hammerslag |
| 2006/0111779 A1 | 5/2006 | Peterson |
| 2006/0111780 A1 | 5/2006 | Petersen |
| 2006/0111781 A1 | 5/2006 | Petersen |
| 2006/0111782 A1 | 5/2006 | Peterson |
| 2006/0142762 A1 | 6/2006 | Michelson |
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0184172 A1 | 8/2006 | Michelson |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0200164 A1 | 9/2006 | Michelson |
| 2006/0206118 A1 | 9/2006 | Kim et al. |
| 2006/0217812 A1 | 9/2006 | Lambrecht et al. |
| 2006/0229625 A1 | 10/2006 | Truckai et al. |
| 2006/0235387 A1 | 10/2006 | Peterman |
| 2006/0235391 A1 | 10/2006 | Sutterlin |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0055245 A1 | 3/2007 | Sasso et al. |
| 2007/0055263 A1 | 3/2007 | Way et al. |
| 2007/0073402 A1 | 3/2007 | Vresilovic et al. ........ 623/17.12 |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park ....................... 623/17.12 |
| 2007/0149976 A1 | 6/2007 | Hale et al. |
| 2007/0149983 A1 | 6/2007 | Link |
| 2007/0150061 A1 | 6/2007 | Trieu ....................... 623/17.12 |
| 2007/0161991 A1 | 7/2007 | Altarac et al. |
| 2007/0179617 A1 | 8/2007 | Brown et al. |
| 2007/0179619 A1 | 8/2007 | Grob et al. |
| 2007/0225721 A1 | 9/2007 | Thelen et al. |
| 2007/0244483 A9 | 10/2007 | Winslow et al. |
| 2007/0276491 A1 | 11/2007 | Ahrens et al. ............ 623/17.11 |
| 2007/0299451 A1 | 12/2007 | Tulkis |
| 2008/0021457 A1 | 1/2008 | Anderson et al. |
| 2008/0108996 A1 | 5/2008 | Padget et al. |
| 2008/0140207 A1 | 6/2008 | Olmos et al. |
| 2008/0161810 A1 | 7/2008 | Melkent |
| 2008/0161929 A1 | 7/2008 | McCormack et al. |
| 2008/0167657 A1 | 7/2008 | Greenhalgh |
| 2008/0177311 A1 | 7/2008 | Winslow et al. |
| 2008/0234758 A1 | 9/2008 | Fisher et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0287955 A1 | 11/2008 | Michelson |
| 2008/0312744 A1 | 12/2008 | Vresilovic et al. |
| 2009/0131986 A1 | 5/2009 | Lee et al. |
| 2009/0177205 A1 | 7/2009 | McCormack et al. |
| 2009/0234397 A1 | 9/2009 | Petersen |
| 2009/0306671 A1 | 12/2009 | McCormack et al. |
| 2009/0312763 A1 | 12/2009 | McCormack et al. |
| 2010/0069912 A1 | 3/2010 | McCormack et al. |
| 2010/0086185 A1 | 4/2010 | Weiss |
| 2010/0093829 A1 | 4/2010 | Gorman |

FOREIGN PATENT DOCUMENTS

| | | |
|---|---|---|
| FR | 2 722 980 A1 | 2/1996 |
| WO | WO 99/49818 A1 | 10/1999 |
| WO | WO 00/35388 A1 | 6/2000 |
| WO | WO 00/53126 A1 | 9/2000 |
| WO | WO 01/01895 A1 | 1/2001 |
| WO | WO 02/34120 A2 | 5/2002 |
| WO | WO 02/38062 A2 | 5/2002 |
| WO | WO 02/076335 A2 | 10/2002 |
| WO | WO 2006/058221 A2 | 6/2006 |
| WO | WO 2006/130791 A2 | 12/2006 |
| WO | WO 2009/089367 A2 | 7/2009 |
| WO | WO 2009/148619 A2 | 12/2009 |
| WO | WO 2010/030994 A2 | 3/2010 |

OTHER PUBLICATIONS

Interview summary, U.S. Appl. No. 11/618,619, mailed Mar. 18, 2008, 3 pages.
Amendment, U.S. Appl. No. 11/618,619, filed May 5, 2008, 10 pages.
Final Office Action, U.S. Appl. No. 11/618,619, mailed Aug. 8, 2008, 10 pages.
Amendment and Response to Non-Final Office Action, U.S. Appl. No. 12/110,548, filed May 5, 2009, 11 pages.
Annex to Form PCT/ISA/206 Communication Relating to the Results of the Partial International Search and p. 1 of the Invitation to Pay Additional Fees, International patent application No. PCT/US2009/030461, dated May 13, 2009, 3 pages.
U.S. Appl. No. 12/317,682, filed Dec. 23, 2008, McCormack et al.

U.S. Appl. No. 12/350,609, filed Jan. 8, 2009, McCormack et al.

Annex to Form PCT/ISA/206 Communication Relating to the Results of the Partial International Search and p. 1 of the Invitation to Pay Additional Fees, International patent application No. PCT/US2009/003423, dated Sep. 14, 2009, 3 pages.

International Search Report and Written Opinion, International patent application No. PCT/US2007/089146, dated Nov. 3, 2008.

International Search Report and Written Opinion, International patent application No. PCT/US2009/030461, dated Aug. 17, 2009.

International Search Report and Written Opinion, International patent application No. PCT/US2009/003423, dated Dec. 14, 2009.

International Search Report, International patent application No. PCT/US2009/056841, dated Apr. 9, 2010.

Press Release, Interventional Spine, Inc., FDA Grants Conditional Approval to Interventional Spine's PercuDyn™ System IDE Application (Jul. 1, 2008).

Press Release, Interventional Spine, Inc., Interventional Spine, Inc. Introduces the PERPOS® Fusion Facet Prep Kit (Oct. 14, 2008).

Press Release, minSURG Corp., Orthopedic Development Corporation's TruFUSE® Procedure Tops 1,750 Patients in First Year (Sep. 24, 2007).

U.S. Appl. No. 12/653,283, filed Dec. 10, 2009, McCormack et al.

International Search Report and Written Opinion, International patent application No. PCT/US2009/006478, dated Jun. 29, 2010.

US 7,063,700, 06/2006, Michelson (withdrawn)

* cited by examiner

CERVICAL DISTRACTION METHOD

CROSS-REFERENCE TO RELATED APPLICATIONS

This application is a divisional application of U.S. patent application Ser. No. 11/618,619 filed on Dec. 29, 2006, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to an implantable distraction device, and more particularly to a cervical distraction device.

2. Description of Related Art

Chronic back problems cause pain and disability for a large segment of the population. Adverse spinal conditions are characteristic of age. With aging, generally comes an increase in spinal stenosis (including, but not limited to, central canal and lateral stenosis), and facet arthropathy. Spinal stenosis results in a reduction of foraminal area (i.e., the available space for the passage of nerves and blood vessels) which compresses the cervical nerve roots and causes radicular pain. Extension and ipsilateral rotation of the neck further reduces the foraminal area and contributes to pain, nerve root compression, and neural injury. However, neck flexion generally increases the foraminal area.

Cervical disc herniations predominantly present with upper extremity radicular symptoms. The vast majority of these herniations do not have an associated neurologic deficit and present with pain only. A well-described treatment for cervical disc herniations is closed traction. There are a number of marketed devices that alleviate pain by pulling on the head to increase foraminal height.

Cervical disc herniations have been treated with anterior and posterior surgery. The vast majority of these surgeries are performed through an anterior approach, which requires a spinal fusion. These surgeries are expensive and beget additional surgeries due to change in biomechanics of the neck. There is a 3% incidence of re-operation after cervical spine surgery.

Therefore, an object of the present invention is to provide a minimally invasive device and surgery to increase foraminal height and reduce radicular symptoms for patients with disc herniations.

At least some of these objectives will be met in the following disclosure.

BRIEF SUMMARY OF THE INVENTION

A device and technique are disclosed for a minimally invasive surgical implantation to reduce radicular symptoms by inserting an expandable cervical distraction implant in the facet joint at an affected level to preserve the physiology of the spine. In particular, embodiments of the present invention provide for distracting the cervical spine to increase the foraminal dimension in extension and neutral positions. The implant of the present invention, when positioned in the cervical facet joint, expands to distract, or increase the space between, the vertebrae to increase the foraminal area or dimension, and reduce pressure on the nerves and blood vessels of the cervical spine.

The procedure may be performed under conscious sedation in order to obtain intra-operative patient symptom feedback.

When the distraction implant is optimally positioned in the facet joint, it is injected with a bio-inert hydrogel using a catheter inflation syringe with pressure/volume monitor. The injection of the hydrogel causes the implant to expand in order to achieve cervical distraction. At this point in the procedure, patient feedback regarding symptom improvement could be obtained.

After achieving the desired distraction, the catheter is detached from the distraction implant and be removed. The patient is left with the distraction implant expanded in the facet joint with permanent increased foraminal height.

One aspect of the invention is an apparatus for distracting first and second adjacent vertebrae. The apparatus has an expandable implant configured to be inserted in a collapsed configuration within a facet joint bounded by the first and second vertebrae, and expand within the facet joint to increase a foraminal dimension, e.g. foraminal height associated with the first and second adjacent vertebrae.

Preferably, the expandable implant is configured to be installed in a facet joint located between at least one cervical vertebra. However, other locations are contemplated.

In one embodiment, the expandable implant is configured to engage the articulating surfaces of the facet joint to increase the distance between the articulating surfaces, the distance correlating to the foraminal dimension.

The expandable implant may comprises an inflatable balloon configured to be filled with an inflation medium, e.g. hydrogel or the like, to distribute a compressive load on the articulating surfaces.

Generally, the facet joint has a joint capsule that extends beyond the margin of the articulating surfaces. In a preferred embodiment, the expandable implant is configured to be delivered into the facet joint through an access hole created in the joint capsule. The expandable implant is ideally configured such that, in its expanded configuration, is larger than the access hole so that the expandable implant is retained in the facet joint once expanded. The expandable implant may also be configured to plug the access hole once expanded. Typically, the expandable implant is configured to occupy a substantial portion of the depth of the facet joint once expanded.

In another preferred embodiment, the expandable implant is configured to dynamically stabilize the facet joint. Generally, the expandable implant increases and maintains a minimum distance between the articulating surfaces, while allowing motion of the first vertebrae with respect to the second vertebrae.

For delivery, the expandable implant preferably attaches to a distal tip of a catheter to facilitate installation into the facet joint. The catheter transports the inflation medium into the expandable implant. The expandable implant is configured to detach from the catheter once the implant is expanded in the facet joint.

Another aspect is a method of minimally invasively distracting first and second adjacent vertebrae. The method includes the steps of inserting an expandable implant, in a collapsed state, into a facet joint bounded by the first and second vertebrae, and expanding the expandable implant within the facet joint to increase a foraminal dimension associated with the first and second vertebrae.

In a preferred embodiment, the expandable implant is installed in a facet joint located between at least one cervical vertebra. The expandable implant engages the articulating surfaces of the facet joint to increase the distance between the articulating surfaces.

In many embodiments, inserting an expandable implant is achieved by creating an access hole through the joint capsule, and inserting the expandable implant in a collapsed configuration through the access hole and into the facet joint. Typically, the access hole is created with an introducer needle used to deliver the expandable member.

In a preferred embodiment, an inflatable balloon is filled with an inflation medium causing the balloon to engage the articulating surfaces the expandable implant. A compressive load is imparted on the articulating surfaces to distract the first vertebra from the second vertebra.

To inflate the expandable implant, a catheter is fed through the access hole and into the facet joint with the expandable implant attached to a distal tip of a catheter. An inflation medium is then delivered into the expandable implant via the catheter to inflate expandable implant with the inflation medium. Once inflated, the expandable implant detaches from the catheter once the implant is expanded in the facet joint.

Dynamic stabilization of the facet joint is affected as a result of the expanded implant being disposed between the articulating surfaces of the facet joint. The distance between the articulating surfaces is maintained while allowing motion of the first vertebrae with respect to the second vertebrae.

In one embodiment, the extent of inflation of the expandable member is determined via patient feedback while the expandable member is being inflated.

Another aspect is a system for distracting a first vertebra from a second adjacent vertebra. The system includes a catheter and an expandable implant configured to be detachably installed in a collapsed configuration on the distal tip of the catheter. The expandable implant and catheter are configured to be inserted in into a facet joint bounded by the first and second vertebrae to expand the expandable implant within the facet joint to increase a neural foraminal height associated with the first and second vertebrae.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 3:
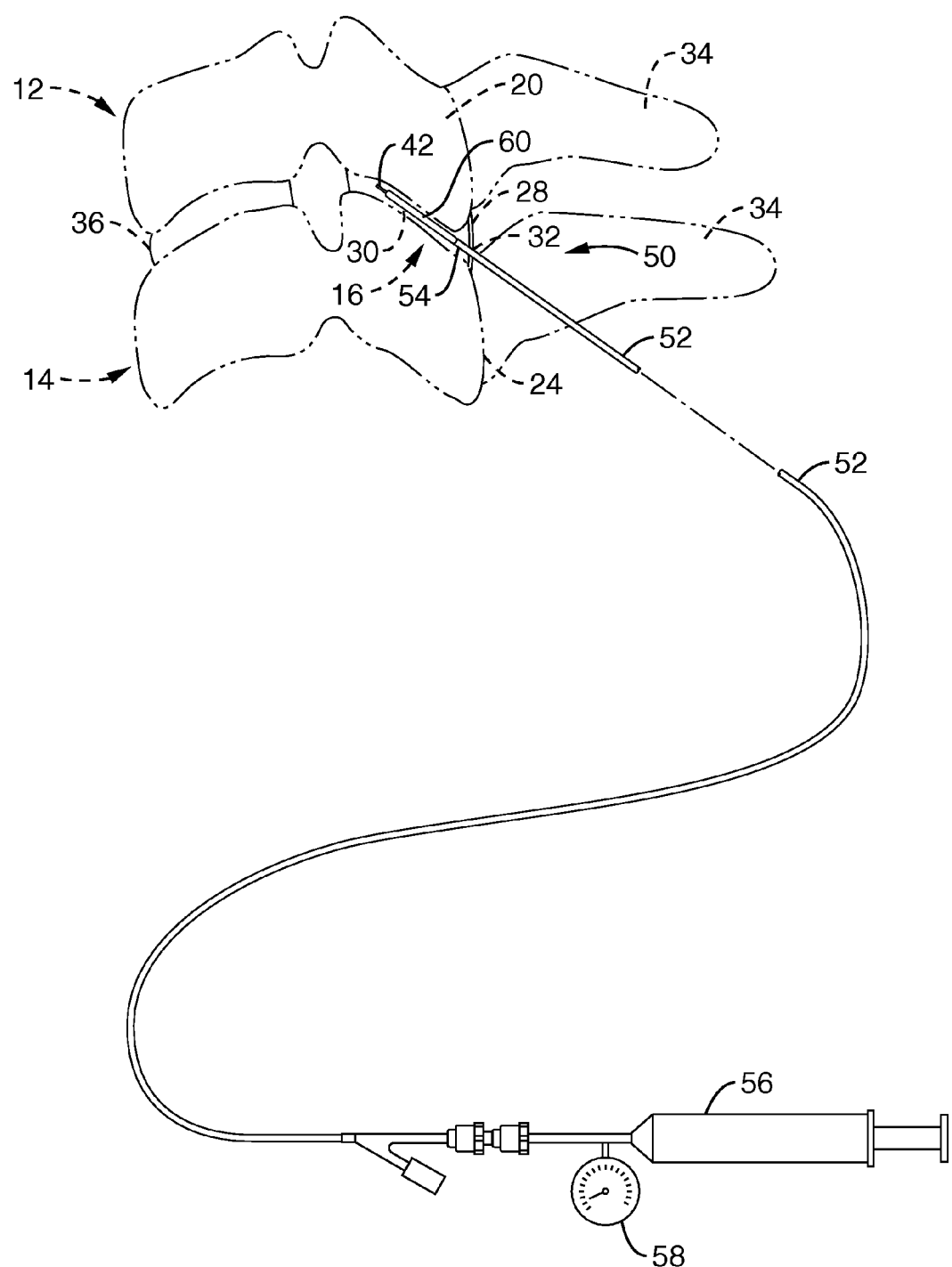
FIG. 3 illustrates an implant of the present invention being inserted into the facet joint.
Figure 4:
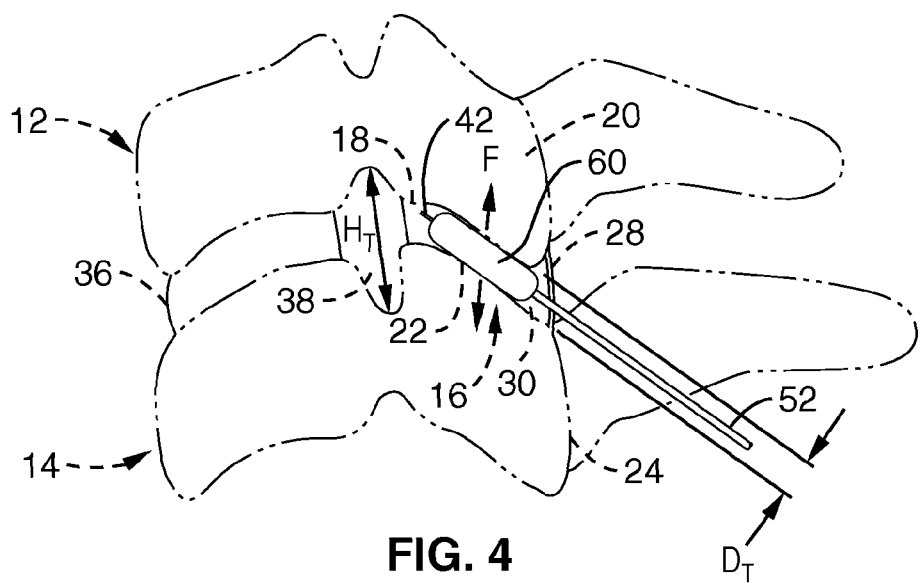

FIG. 4. illustrates the implant of FIG. 3 in an expanded configuration.

Figure 5:
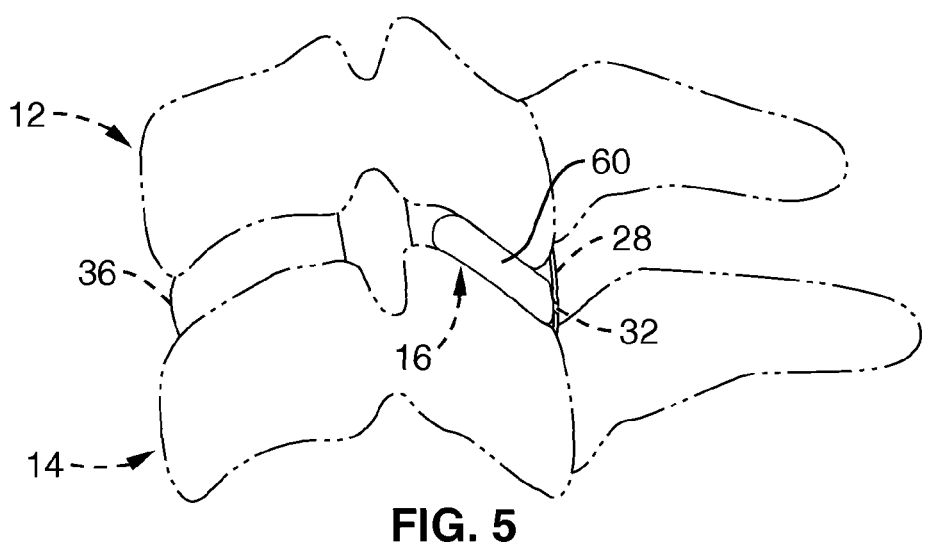

FIG. 5 illustrates the implant of FIG. 4 with the catheter detached from the implant and removed from the treatment site.

Figure 6:
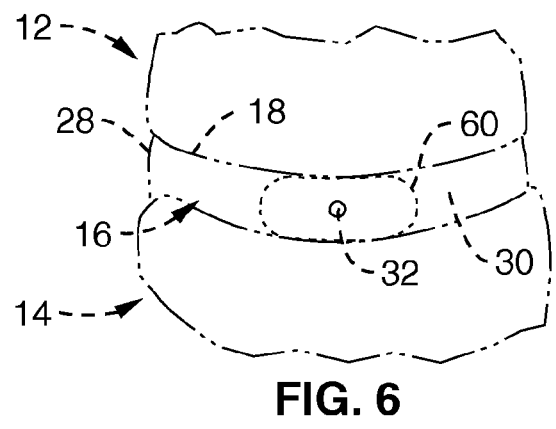

FIG. 6 is another view of the placement of the implant in the facet joint in accordance with the present invention.

Figure 7:
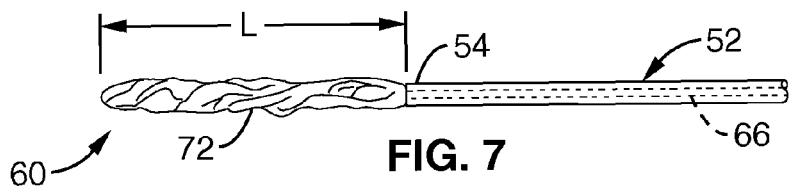

FIG. 7 is an expanded view of the implant installed in a collapsed configuration on a catheter.

Figure 8:
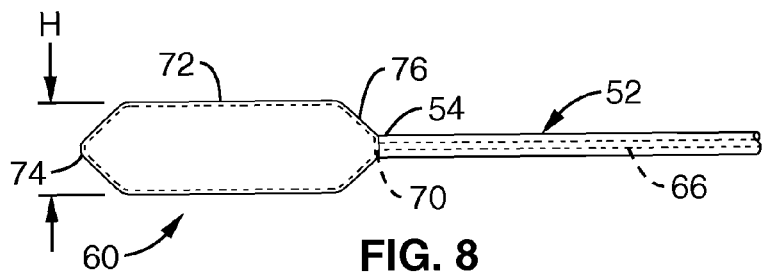

FIG. 8 illustrates the implant of FIG. 7 in an expanded configuration.

Figure 9:
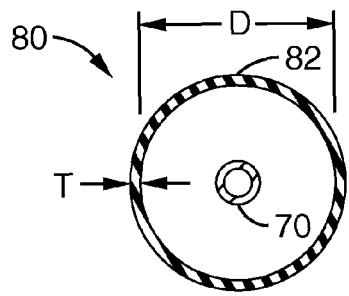

FIG. 9 illustrates an implant of the present invention having a circular cross-section.

Figure 10:
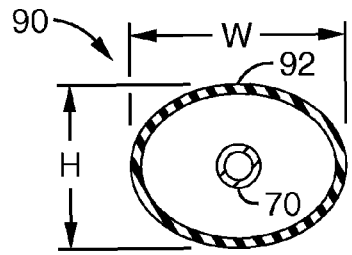

FIG. 10 illustrates an implant of the present invention having an oval cross-section.

Figure 11:
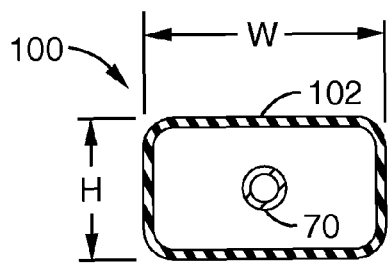

FIG. 11 illustrates an implant of the present invention having a rectangular cross-section.

Figure 12:
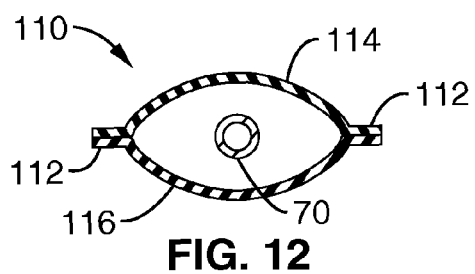

FIG. 12 illustrates an implant of the present invention having 2-piece design.

Figure 13:
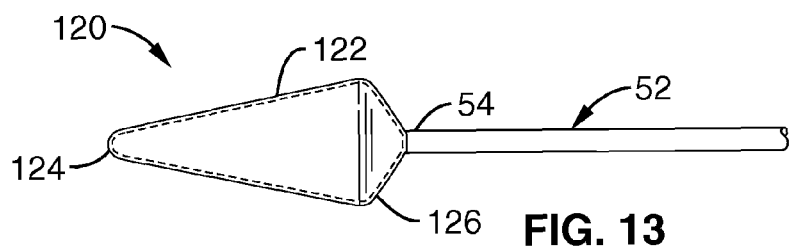

FIG. 13 illustrates an implant of the present invention having a taper along its length.

DETAILED DESCRIPTION OF THE INVENTION

Referring more specifically to the drawings, for illustrative purposes the present invention is embodied in the apparatus generally shown in FIG. 2 through FIG. 13. It will be appreciated that the apparatus may vary as to configuration and as to details of the parts, and that the method may vary as to the specific steps and sequence, without departing from the basic concepts as disclosed herein.

Figure 1:
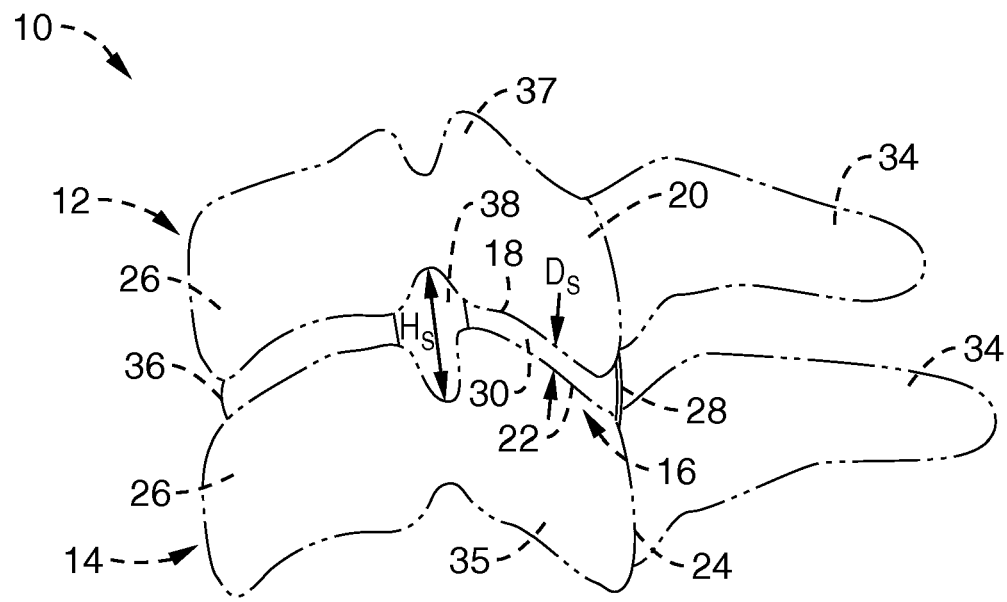
FIG. 1 is a lateral view of two cervical vertebral members in a stenosed condition.

FIG. 1 illustrates a simplified lateral view of a portion of the cervical spine 10. The basic biomechanical unit or motion segment of the spine consists of two adjacent vertebrae 12 and 14 and the three joint articular complex through which they move and are constrained in relation to one another. The spine articulations generally consist of an intervertebral disc 36 located between the vertebral bodies 26 of adjacent vertebrae 12, 14, and two facet joints 16 symmetrically located laterally from the sagittal plane at the posterior end of the vertebral bodies 26.

The facet joints 16 allow constrained spinal motion, while protecting the contained neural structures. From a kinematic viewpoint, the intervertebral facet joints 16 are highly constrained sliding planar articulations, lubricated by synovial fluid contained within the facet joint capsule 30. In the cervical spine, the geometry of the cervical vertebral bodies provides a high degree of protection for the neural elements by limiting normal motion of the spine to within physiologic limits. The upward inclination of the superior articular surfaces of the facet joints allows for considerable flexion and extension, as well as for lateral mobility.

Minimally invasive surgical access to the facet joint is well documented. Each vertebral segment comprises a spinous process 34 located at the posterior end of the vertebrae, with the vertebral body located anteriorly. Each vertebra comprises an inferior articular (or transverse) process 35 and the superior articular process 37 that form four posterior articulating, e.g. opposing subchondral, surfaces: two superior facets 18 and two inferior facets 22. The superior facet 18 from the inferior articular process 35 of the upper vertebra 12 and the inferior facet 22 from the superior articular process 37 of the lower vertebra 14 form the facet joint 16 on each lateral side of the spine.

Located medial to the articular processes 37 and vertebral bodies 26 is an aperture, or intervertebral foramina 38, that serves as a nerve root canal for the spinal nerves and vessels that transmit signals from the spinal chord to respective locations in the body.

Each facet joint 16 is covered by a dense, elastic articular capsule 28, which is attached just beyond the margins of the articular facets 18, 22. The inside of the capsule is lined by a synovial membrane (not shown) which secretes synovial fluid for lubricating the facet joint. The exterior of the joint capsule is surrounded by a capsular ligament (not shown), which may be temporarily repositioned to give access for insertion of the extendable implant of the present invention, described in further detail below. Thus, from a posterior-lateral approach, access to the facet joint 16 is relatively straightforward and well prescribed, as compared to other regions of the spine which present a higher likelihood of trauma and risk of permanent damage.

It should also be noted that FIG. 1 depicts cervical foraminal stenosis, e.g. loss of height between the adjacent vertebrae 12, 14. As a result of disc 36 herniation and corresponding height loss, the nerve root canal 38, or intervertebral foraminal height, having a value $H_S$, is narrowed relative to that of healthy anatomy. This narrowing of the foraminal height $H_S$ often leads to compression of the spinal cord and nerve roots (not shown), causing radicular symptoms.

As a result of the stenosed foraminal height $H_S$, the height of the facet joint 16, or distance between subchondral articulating surfaces 18 and 22, is also narrowed, (shown as value $D_S$ in FIG. 1). This may pose complications in the facet joint 16 as well. However, more importantly, because the height of the disc will be relatively fixed, an increase in the facet joint height will also have a corresponding increase in foraminal height, as described in greater detail below.

FIGS. 2-6 show the methods and system 50 of the present invention for performing a minimally invasive procedure configured to distract one or more of the facet joints 16 of vertebrae 12, 14, thereby increasing the dimension of the neural foramen while retaining facet joint mobility. One of the major advantages of minimally invasive surgery is the ability to perform the procedure with minimal tissue trauma. Television image intensifier fluoroscopy may be used to provide guidance for surgeon placement of instrumentation and implants precisely to the desired anatomic target in the facet joint 16. The radiographic landmarks are well taught and the relative procedural difficulty of this technique is low.

Figure 2:
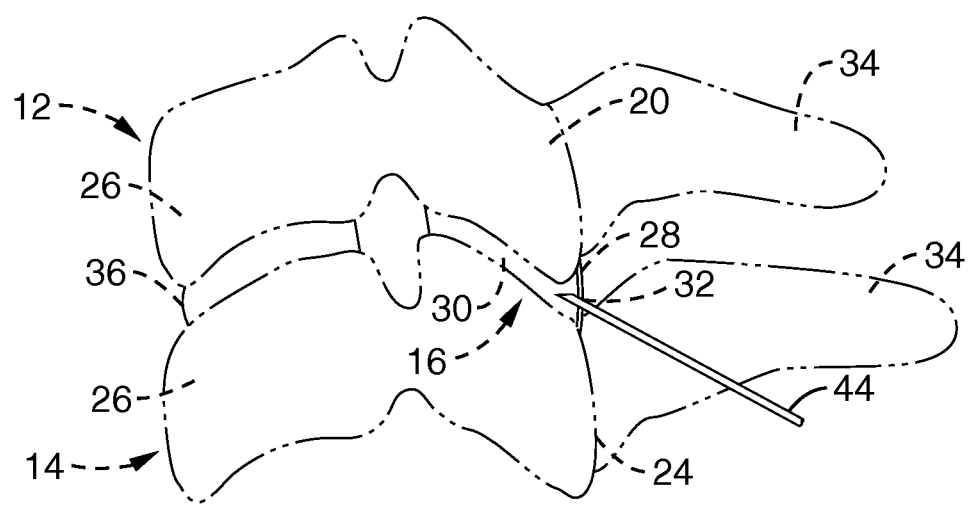
FIG. 2 is a view of an introducer needle being inserted into the facet joint of the vertebral members in accordance with the present invention.

Referring to FIG. 2, a standard discography introducer needle 44 (e.g. approximately 21 gauge needle) is inserted into the outer facet capsule 28 to create a perforation or access hole 32 into the facet joint cavity 30. Dye may then be injected through the introducer needle 44 to fluoroscopically confirm that the introducer needle 44 is in the facet joint cavity 30.

Referring now to FIG. 3, a catheter 52 having an expandable implant 60 coupled to the distal end 54 of the catheter 52, may then be guided over into the facet joint cavity 30 through needle 44 such that the distal tip 42 of the implant is located in the proper position in cavity 30.

Once the implant 60 is placed at the correct location of the facet joint 16, the implant is injected with a bio-inert hydrogel to inflate the catheter. Inflation may be achieved with a catheter inflation syringe 56, and the pressure and/or volume may be observed via monitor 58. Further visualization may be achieved by including a contrast dye within the hydrogel. The hydrogel and expandable balloon may be similar to the materials found in the HyperGlide Occlusion Balloon Catheter by Micro Therapeutics, Inc., used for vascular occlusions.

FIG. 4 illustrates the implant 60 in an expanded configuration within the facet joint. As shown in FIG. 4, the hydrogel-inflated expandable implant 60 generates an outward compressive force F on the subchondral surfaces 18 and 22 to increase the distance between them to a desired treatment or nominal value $D_T$. This correspondingly increases the height of the intervertebral foramin to a treatment or nominal value $H_T$. The value of $D_T$, and resulting increase in $H_T$ may be predetermined by the surgeon prior to the surgery based on pre-op analysis of the patient's condition and anatomy, and/or may also be iteratively devised by patient feedback of symptom improvement during the procedure.

The size of implant 60 is configured to distract the joint and reverse narrowing of the nerve root canal 38 and alleviate symptoms of cervical stenosis. However, it is also within the scope of the present invention to size the implant according to other spinal conditions, for example to correct for cervical kyphosis or loss of cervical lordosis.

Once the desired inflation/distraction is achieved, the catheter 52 is detached from the implant 60, and fed out of the patient's body. Referring now to FIG. 5, the expanded implant 60 will occupy the joint cavity 30 such that it will occlude the opening 32 in the facet capsule 28. Because the inflated implant 60 is larger than the opening 32 caused by the violation of the joint by the introducer needle 44, the implant 60 acts as a plug to close off the joint cavity 30. In addition, because the implant is confined within the boundaries of the joint cavity 30, including the facet surfaces 18, 22 and capsule 28, it will remain in its installed position without further anchoring to hold the device in place. Due to the properties of synovial joints and the configuration of the implant 60, it is unlikely that the implant 60 will extrude from the joint once it has been implanted. If further constraint is desired, the external walls of the balloon may be fabricated to have a surface roughness or texture configured to inhibit motion with respect to the walls 18, 22 of the facet joint.

If symmetrical distraction is desired between the adjacent vertebrae, the procedure may be repeated for the second facet joint located between the target vertebrae. However, it is contemplated that only one implant may be necessary to alleviate radicular symptoms.

FIG. 6 illustrates a preferred placement of the implant 60 within the facet joint 16. The average width of the cervical facet is approximately 9 mm. The average depth of the cervical facet is also approximately 9 mm. The preferred location of the capsule is generally the center third of the facet joint cavity 30, as its approximate size will be about 3-4 mm in width, as shown in FIG. 6. The length of the implant 60 will be approximately 8-9 mm, or roughly the depth of the facet joint cavity 30, and therefore may preferably occupy all or nearly all of the joint depth. Preferably, the implant 60 will be configured to expand to up to a height of approximately 3 mm or more. It is appreciated that the above sizing of the implant may vary accordingly to accommodate patient anatomy, condition, or desired foraminal height increase or other preferences defined by the surgeon.

The size, configuration, and placement of implant 60 are configured to provide distraction of the facet joint, while also preserving the mobility between the adjacent vertebrae 12, 14. For example, translation of the articular surfaces 18, 22 with respect to each other (e.g. along the plane of the surfaces) is not restrained, while the undesired translation normal to the articular surfaces 18, 22, (e.g. collapsing), is inhibited. Additionally, the adjacent vertebrae 12, 14 are allowed to rotate about the long axis of the implant 60 with respect to each other, as well as rotate about the spinal column axis. Thus, the implant 60 of the present invention allows for dynamic stabilization and distraction of the facet joint to increase and maintain foraminal height.

FIG. 7 illustrates an expandable balloon implant 60 in a collapsed configuration and attached to distal end 54 of catheter 52. The walls 72 of the balloon may be folded over along the length L of the balloon to minimize the profile of the balloon 60.

FIG. 8 illustrates expandable balloon implant 60 in its expanded configuration. Balloon implant 60 is generally comprised of one or more exterior walls that are configured to hold and retain the inflatable medium, e.g. hydrogel. In some embodiments, the implant 60 may have a central lumen (not shown), emanating at proximal end 76, and terminating at distal end 74 through the length L of the balloon. The central lumen allows the implant 60 to be fed over a guide wire, or like device, to the target location in the facet joint 16.

The proximal end 76 will also have a port 70 allowing flow of the inflation medium into the bladder of the balloon. This port 70 may be self-sealing, wherein the port automatically seals upon detaching catheter 52, or may incorporate a plug (not shown) or other sealing mechanism that may be fed over guide wire 40 to close and seal up port 70 once the catheter 52 is removed.

The cross section of the implant may comprise a variety of different shapes, as shown in FIGS. 9-12. In FIG. 9, balloon implant 80 comprises an outer wall 82 having a generally circular shape, thus creating a cylindrical structure across the length of the balloon. The thickness T of the external wall 82 is configured to withstand the compressive loads associated with the facet joint in the cervical spine, and may be varied accordingly. With the cylinder shape implant 80, the outer wall will generally contact and engage the facet surfaces 18, 22 in a line down the depth of the facet cavity 30. The diameter D of the outer wall 82 will be sized for the desired increase of the foraminal height, e.g. ranging from approximately 1 mm to over 3 mm.

As illustrated in 10, balloon implant 90 may comprise a elliptical or oval cross section, having a height H sized for desired increase of the foraminal height, and width W. A rectangular cross section may also be used, as shown with implant 100 of FIG. 11.

The implants 80, 90 and 100 may be fabricated by a number of methods currently available in the art. For example, the implant may be formed as a single piece structure over a mandrel (not shown) having varying cross section for the central lumen (if needed) and outer walls 82, 92, 102.

In an alternative embodiment shown in FIG. 12, the balloon 110 may comprise a bladder having upper wall 114 and lower wall 115 that are heat sealed at the sides 112.

As illustrated in FIG. 13, the balloon may also be tapered along its length to accommodate the anatomy of the facet joint 16, as seen with balloon 120, wherein the leading or distal end 124 has a smaller profile than the trailing or distal end 126.

The extendable implants above may comprise an elastic material, e.g. biocompatible polymer, which allows the implant to expand to a varying range in sizes. Alternatively, the implant may comprise an inelastic material that has a maximum inflation capacity, and wherein a number of predetermined sizes may be available to the surgeon according to the desired size determined by the surgeon.

The implant 60 will generally be sized to accommodate the geometry of the patient anatomy and target foraminal height. For cervical herniations, the implant 60 will typically be installed from the C4/C5 joint down to C7/T1 (95% of all cervical herniations occur at C5/6 & C6/7). The height of the implant 60 may range from approximately 1 mm to over 3 mm, depending on the patient anatomy. For the cylindrical-shaped balloon 80 of FIG. 9, the width will roughly equal the height. However, as shown in FIGS. 10-12, the width may be increased for the desired stabilizing effect.

Although the embodiments disclosed above are directed primarily to installation in the cervical facet joint, it is contemplated that the devices and methods may also be used to increase foraminal dimension in other regions of the spine, e.g. thoracic, lumbar, etc.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for increasing foraminal height between first and second adjacent vertebrae of a patient under conscious sedation, the adjacent vertebrae having a facet joint comprising opposing articulating surfaces of adjacent vertebrae and a joint capsule that extends beyond the margin of the articulating surfaces, the opposing articulating surfaces having a shape and a relative orientation defining a geometry of a patient anatomy, the method comprising:

determining the geometry of the patient anatomy;

selecting an implant from a plurality of inflatable implants, each implant comprised of an inelastic material, wherein a geometry of the selected implant corresponds to the geometry of the patient anatomy and an intended reversal of narrowing of a nerve root canal of the patient;

creating an access hole through the joint capsule with an introducer needle;

injecting dye through the introducer needle;

fluoroscopically confirming that the introducer needle is positioned in the facet joint;

inserting the selected implant through the needle and into the facet joint with a catheter, the selected implant being in a collapsed configuration and being connected to a distal end of the catheter;

positioning the selected implant such that the geometry of the selected implant corresponds to the geometry of the patient anatomy;

inflating the selected implant within the facet joint by advancing a bio-inert hydrogel through the catheter and into the selected implant with a catheter inflation syringe, the hydrogel including a contrast dye;

monitoring the inflating via a monitor positioned on the syringe;

fluoroscopically monitoring the inflating via the contrast dye in the hydrogel;

obtaining intra-operative patient feedback regarding symptom improvement;

iteratively adiustinq the inflating of the selected implant according to patient feedback.

2. A method as recited in claim 1, wherein the selected implant in the fully inflated configuration retains the increased foraminal dimension while allowing motion of the first vertebrae with respect to the second vertebrae.

3. A method as recited in claim 1, wherein the selected implant, in the inflated configuration, has a length corresponding to the depth of the facet joint, and a height corresponding to the desired distraction of the facet joint height to achieve said increased foraminal dimension.

4. A method as recited in claim 3:
wherein, in the inflated configuration, the length of the selected implant occupies the majority of the facet joint depth; and
wherein the width of the selected implant occupies at least the center third of the facet joint width.

5. A method as recited in claim 1, wherein the patient feedback is used to set the fully inflated height of the selected implant.

6. The method as recited in claim 1, wherein the selected implant includes a self sealing mechanism at the connection to the catheter, the method further comprising detaching the catheter from the selected implant and withdrawing the catheter.

7. The method as recited in claim 1, wherein the implant includes a central lumen and inserting the selected implant includes advancing the selected implant and catheter over a guide wire.

8. The method as recited in claim 1, wherein the selected implant has a tapered shape adapted to accommodate the geometry of the patient anatomy.

* * * * *